United States Patent [19]

Amendolia

[11] Patent Number: 4,515,588
[45] Date of Patent: May 7, 1985

[54] I.V. FLOW REGULATOR

[75] Inventor: Pasquale J. Amendolia, St. James, N.Y.

[73] Assignee: Health Care Concepts, Inc., Allamuchy, N.J.

[21] Appl. No.: 495,058

[22] Filed: May 16, 1983

[51] Int. Cl.³ .............................................. A61M 5/00
[52] U.S. Cl. .................................... 604/118; 604/247; 128/DIG. 12
[58] Field of Search .............................. 604/245–247, 604/118, 141, 9, 30, 31, 207, 237, 248, 249, 323, 151–153, 324, 34, 256; 128/DIG. 12, DIG. 13; 137/501

[56] References Cited

U.S. PATENT DOCUMENTS

| | | | |
|---|---|---|---|
| 4,142,523 | 3/1979 | Stegeman | 604/246 |
| 4,364,386 | 12/1982 | Jenkins | 604/31 |
| 4,468,222 | 8/1984 | Lundquist | 604/153 |

Primary Examiner—Stephen C. Pellegrino
Assistant Examiner—Mark D. Rooney
Attorney, Agent, or Firm—Leonard Belkin

[57] ABSTRACT

A flow regulator for use in an I.V. administration arrangement which establishes and maintains the rate of liquid flow regardless of changes in head which may occur. The regulator utilizes a diaphragm controlled orifice and a bypass with a valve to establish the flow rate. The diaphragm adjusts the effective orifice opening to maintain constant the flow selected by the valve.

11 Claims, 15 Drawing Figures

I.V. FLOW REGULATOR

BACKGROUND OF THE INVENTION

This invention relates to apparatus for regulating the flow of a liquid being delivered to a patient such as in the administration of intravenous (I.V.) solutions, and more particularly to disposable flow regulation apparatus which will maintain a preselected rate of flow which will not be altered by changes in elevation of the point of administration or level of the supply liquid.

The administration of glucose, saline, or other solutions with or without pharmaceuticals to patients in hospitals or elsewhere is a common mode of treatment capable of fulfilling a variety of medical requirements.

In a typical arrangement for such administration there is utilized a stand for supporting a reservoir containing a measured amount of the liquid, tubing extending down from the reservoir, and, for intravenous feeding, an implement which would include a needle attached to the end of the tube for delivering the liquid into the body of the patient.

The reservoir is ordinarily held well above the point of administration so that gravity is relied upon to provide the necessary pressure to insure continuous flow of the liquid. A valve in the tubing not only permits fluid flow to be initiated or terminated at will, but also regulates the rate of flow so that the nurse or other medical technician can set the rate of flow as prescribed by the attending physician. Customarily a drip chamber is provided to permit clear visualization of the rate of flow by counting the number of drops per unit of time.

One of the problems associated with the arrangement just described has to do with certain variable conditions which in effect cause the rate of flow of the liquid to change after it has been set. The flow rate is a function of the head, that is, the differential height between the point of administration and the effective level of the liquid supplying the connecting tubing. If the patient moves his arm (if administration is to his arm) vertically by raising or lowering it, if the level of the liquid supply changes, or if supply is moved to transport or move the patient, there is a change in head which results in a marked alteration in the rate of flow. A technician can be called upon to readjust the valve to continue the same rate of flow, but in many cases the appropriate hospital personnel may not be available, and in any event such a procedure is inefficient and awkward.

This problem has been recognized, and there have been and are a variety of attempts to overcome such a difficulty.

In U.S. Pat. No. 4,043,332, there is shown an arrangement which utilizes pressurization of the solution in combination with a diaphragm-controlled orifice with an adjustable bypass to obtain a differential pressure across the diaphragm to obtain a constant flow rate. Aside from being bulky and expensive in construction, making it unsuitable for large scale application in a busy hospital environment, the patented arrangement has been found to be ineffective for use in I.V. systems where relatively low pressures are involved. In addition, the idea of connecting a pressurized system to the blood vessel of a patient is not attractive to medical practitioners.

U.S. Pat. No. 4,142,523 discloses a flow control device which employs a membrane to control an orifice discharging the liquid, the membrane forming two liquid chambers, and a bypass arrangement with a valve to permit selection of the desired rate of flow. The membrane maintains the flow constant. In this patent, the design is unnecessarily complex, and there is some question whether the particular membrane construction will produce the fixed degree of control desired. The patentee visualizes reuse of the device as a replaceable filter is provided.

SUMMARY OF THE INVENTION

The present invention overcomes or reduces many of the problems of previous systems for regulating the flow rates of liquids being administered to patients by providing a system incorporating a safe, reliable, and effective regulator for maintaining constant flow at a selected rate regardless of changes in fluid pressure caused by changes in fluid levels. Due to simplicity of the design, the regulator in accordance with this invention may be discarded after a single use.

In accordance with a preferred embodiment of this invention, there is provided a gravity feed system for such liquids consisting of a reservoir containing a supply of the liquid, and tubing connecting the reservoir to the injection device with the reservoir held above the level of administration to obtain the gravity feed. In the tubing, a liquid flow regulator is incorporated which embodies the principles of this invention. The regulator consists of a housing with an inlet and outlet, with a diaphragm having a membrane for separating the inlet from the outlet, and dividing the interior of the housing into inlet and outlet chambers, respectively. Liquid from the reservoir enters the housing through its inlet and leaves through its outlet on its way through the tubing to the injection device.

The outlet has an orifice opening, and the membrane is located sufficiently close to the opening so that movement of the former to and away from the orifice opening will control flow of liquid through the outlet. A passageway for communicating between the two chambers is provided through the diaphragm but bypasses the membrane, and a valve device is present to select the rate of flow of liquid through the passageway and hence to the injection device. Differential pressure across the membrane by the liquid in both chambers acts to maintain a constant flow through the passageway by adjusting the effective opening through the orifice opening to compensate for changes in the head due to vertical movement of the patient or the liquid level supply.

It is thus a principal object of this invention to provide a gravity flow system for delivering a liquid for administration to a patient and maintaining a selected rate of flow.

Another object of this invention is to provide a liquid flow regulator which maintains a selected rate of flow in spite of changes in pressure within the liquid.

Other objects and advantages of this invention will hereinafter become obvious from the following description of preferred embodiments of this invention.

BRIEF DESCRIPTION OF THE DRAWINGS

FIG. 10 is a view looking down on the diaphragm shown in FIG. 9a.

DESCRIPTION OF THE PREFERRED EMBODIMENTS

Figures 1, 2, 3:
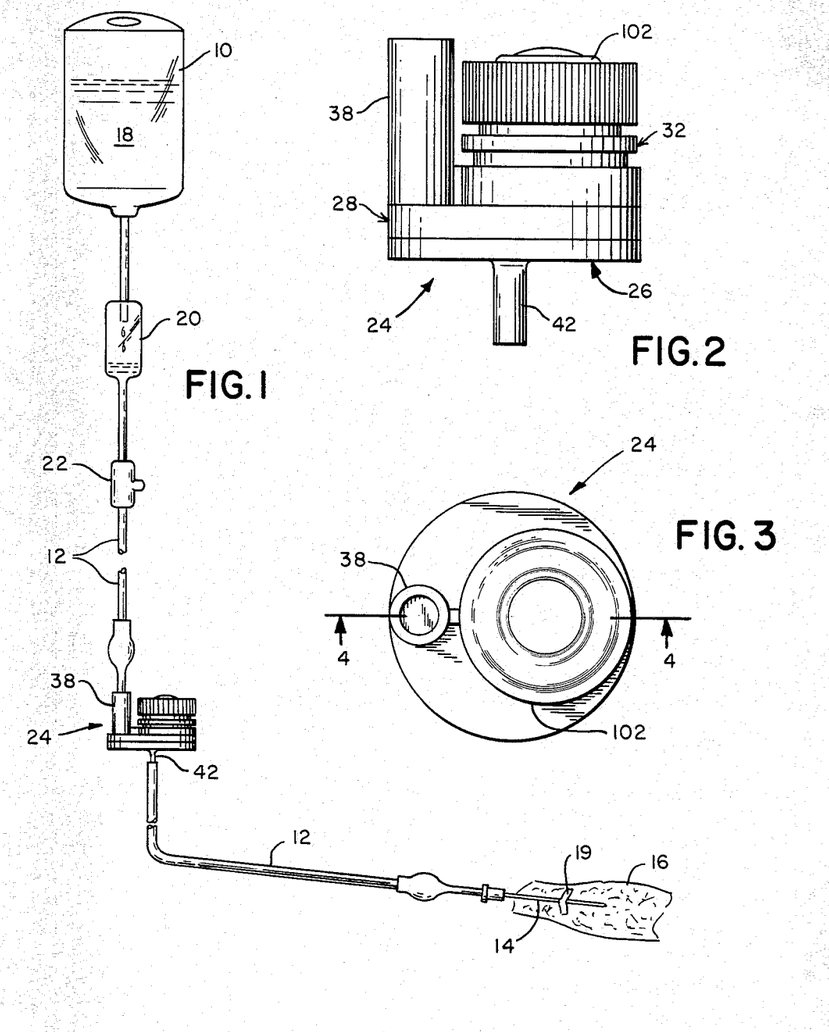
FIG. 1 is a partially schematic view of an I.V. administration system embodying the principles of this invention.
FIG. 2 is an elevation view of the regulator shown in FIG. 1.
FIG. 3 is a plan view of the regulator illustrated in FIG. 2.

An I.V. administration system forming a preferred embodiment of this invention consists, as shown in FIG. 1, of a reservoir 10 connected through tubing 12 to a hypodermic needle 14 which is inserted into the arm 16 of a patient for the delivery of the parenteral liquid 18 stored in reservoir 10. Tape 19 may be employed to hold needle 14 in place during use.

Tubing 12 is provided with a drip chamber 20, a flow control valve 22, and the flow regulator 24 which incorporates the novel features of this invention.

Reservoir 10 may be a rigid container which is vented so that air can replace liquid 18 as it drains out or may be a sealed collapsible bag where no venting is required.

Drip chamber 20, being of transparent material, as is understood in the art, performs the primary function of permitting the calculation of flow rate by the counting of drops, although it also may serve to remove any air bubbles which might be present in the liquid.

Flow control valve 22 permits the adjustable clamping of tubing 12 passing through, and conventionally it is used to establish the drip rate at the desired value. When regulator 24 is employed, however, valve 22 is used only to initiate or stop flow. That is, valve 22 is either fully open or fully closed. As will be understood from the description and operation of the preferred embodiments of this invention, flow control valve 22 could be dispensed with entirely when a regulator 24 embodying the principles of this invention is employed.

Figure 4:
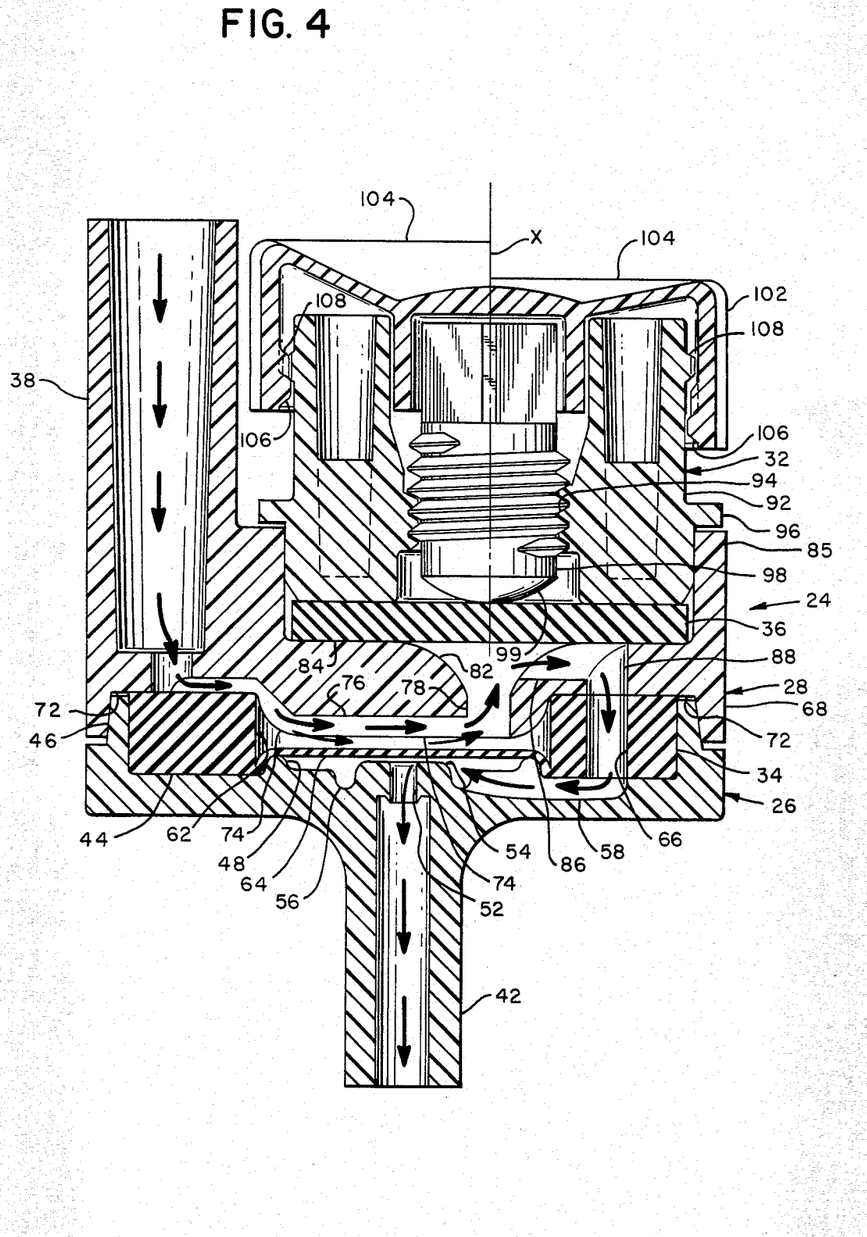
FIG. 4 is a view along 4—4 of FIG. 3.

For details of regulator 24, reference is made to FIGS. 2, 3, and 4. Regulator 24 consists of a diaphragm cap 26, a main body 28, and a valve assembly 32. An orifice control diaphragm 34 is fitted between cap 26 and body 28. A second diaphragm 36 is fitted between body 28 and valve assembly 32. Inlet 38 on body 28 receives liquid passing through regulator 24 while outlet 42 extending from cap 26 discharges liquid passing through this device.

Figure 5:
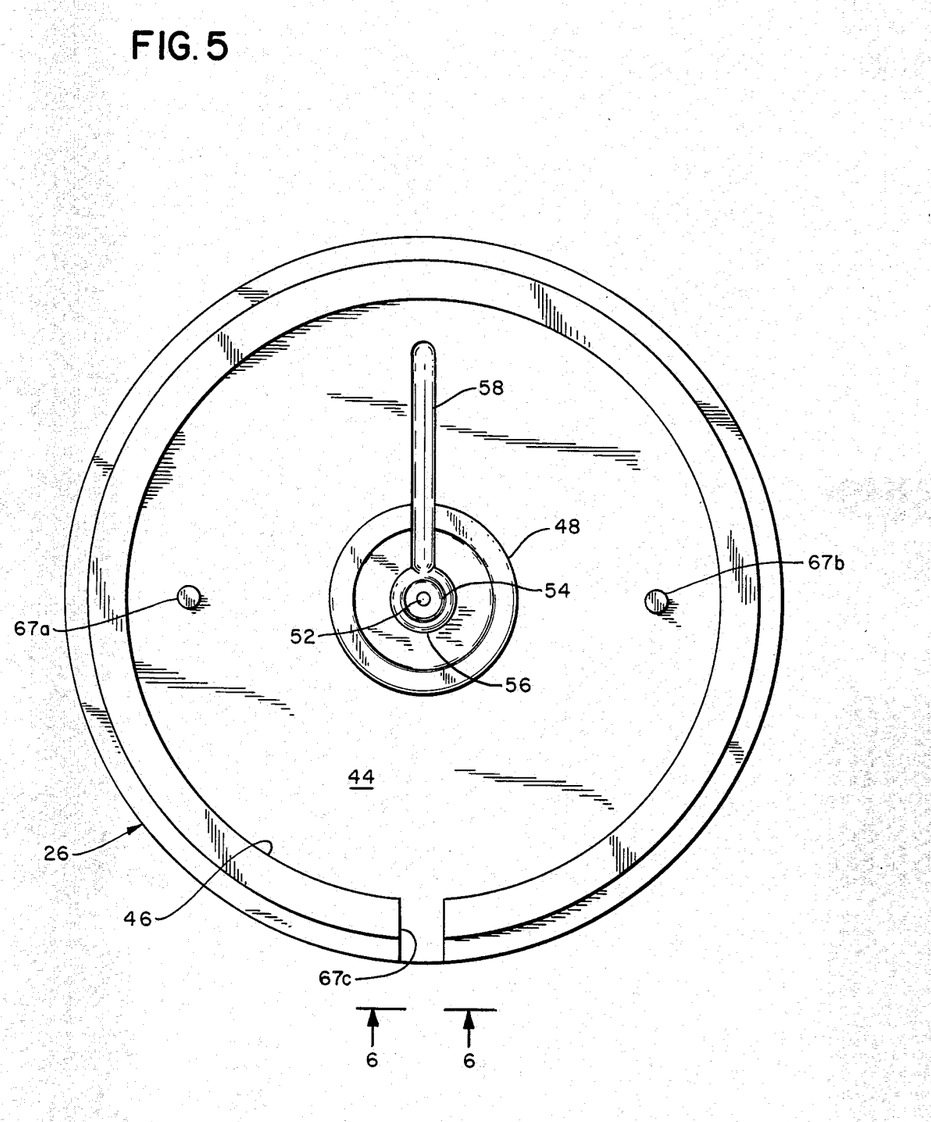
FIG. 5 is a plan view of the diaphragm cap.
Figure 6:
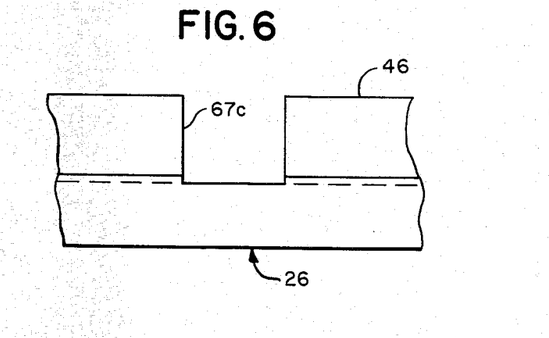
FIG. 6 is a view along 6—6 of FIG. 5.

Cap 26 is disc shaped with outlet 42 extending from one side. As also seen in FIGS. 5 and 6, the other side is provided with an annular groove or trench 44 surrounded by an annular shoulder 46 on the outside and a shorter bulge 48 on the inside. Annularly within the latter there is provided a passageway 52 through an annular bulge or protruding rim 54 to outlet 42 to form an orifice controllable by diaphragm 34 as will be more particularly explained below. The surface between bulges 48 and 54 is generally recessed with an annular groove 56 to form a reservoir below diaphragm 34 and also to perform another function which will become apparent. A passageway 58 communicates with and extends radially from groove 56 to help carry out that function.

Figure 7:
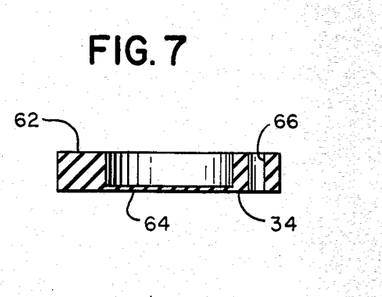
FIG. 7 is a section view through the orifice control diaphragm.

Diaphragm 34, as also seen in FIG. 7, has a thickened rim 62 and a central thin section or membrane 64, and an aperture 66 passing through rim 62. When inserted in cap 26 as illustrated in FIG. 4, thin membrane 64 is stretched over bulge 48, being rendered taut thereby, and is close to but spaced from bulge 54. The thickened rim 62 on diaphragm 34 insures proper location and tautness of the membrane 64 when in place plus makes the apparatus easier and more economical to assemble. Differential liquid pressure acting on membrane 64 will act to control flow of liquid entering passageway 52. For example, a bulging downwardly of membrane 64 will tend to restrict flow, and vice versa. A more detailed description of the operation of membrane 64 will be given below.

Diaphragm 34 is set into cap 26 with aperture 66 lined up with passageway 58 thus effectively providing communication between the two liquid chambers formed by diaphragm 34. Some provision can be made to insure proper alignment of diaphragm 34 in cap 26, such as by the use of two or more projections 67a and 67b on the bottom of trench 44 of cap 26 and matching indents (not shown) in rim 62 of diaphragm 34. A slot 67c in shoulder 46 may be employed to facilitate proper alignment of body 28 when inserted. The latter would be provided with a properly fitted projection (not shown) for this purpose.

Main body 28 is provided with an annular outer extension 68 to engage with shoulder 46 of cap 26, an annular depression 72 to clamp down the thickened rim 62 of diaphragm 34, and a central section 74 which extends toward but is spaced from diaphragm 34 to form a liquid inlet chamber above membrane 64. A radially extending groove 76 forms a passageway between the interior of inlet 38 and a hole 78 having a flared upper portion 82 terminating in a flat section 84 on which flat, disc-shaped diaphragm 36 is located. Section 84 is surrounded by a shoulder 85 to locate the positioning of diaphragm 36.

A radially extending groove 86 forms a passageway between hole 78 and opening 88 which is aligned with aperture 66 in the rim of 62 of diaphragm 34.

It will be seen that selective distortion of diaphragm 36 downwardly in its center section, caused by an arrangement to be described below, will determine the rate of flow of liquid through passageway 86 and ultimately through regulator 24 as will be seen from the description of its operation further below.

Valve assembly 32 consists of a body 92 having a threaded opening 94 and is in contact with diaphragm 36 as is illustrated. Body 92 engages and is attached to shoulder 85 of body 28. A screw member 98 with a hemispherical tip 99 is located within threaded opening 94 and is in contact with diaphragm 36 as shown. A knurled knob 102 with a flexible central section 104 is fitted over to the other end of screw member 98 and extends over body 92 in the manner illustrated. Knob 102 is provided with protuberances 106 which are normally engaged with protuberances 108 on body 92. Knurled knob 102 is normally kept from rotation by the engagement of protuberances 106 and 108 as shown on the left side of the section line X. When it is desired to move screw member 98, in either direction, knob 102 is depressed as shown on the right side of section line X so that the protuberances 106 and 108 are offset from each other, and knob 102 along with threaded member 98 can be rotated to either move the latter downwardly to restrict flow further or upwardly to increase flow. Knob 102 returns to its locked position upon being released due to the elastic nature of its construction.

At the points of engagement between cap 26 and main body 28, that is, shoulder 46 and extension 68 and between main body 28 and body 92 of valve assembly 32, attachment may be accomplished by any conventional means, such as the use of cement, or heat sealing if the material is thermoplastic, or the use of ultrasonic welding. The rigid members as described would be made of any convenient inert material such as a suitable plastic, which could be transparent, and the diaphragms would be constructed of suitable material which would also be inert in the particular environment to which they would be exposed, such as one of any number of natural or synthetic rubbers which are commercially available.

In the operation of the apparatus just described, referring to FIG. 1, valve 22 is in its closed position, and regulator 24 is inserted into tubing 12 at any convenient point between drip chamber 20 and needle 14. Any location is suitable except that it should be located below the level of supply to obtain pressure due to gravitation to operate regulator 24. Inlet 38 on main body 28 receives flow from chamber 20 and outlet 42 discharges flow to needle 14. Conventional adapters are employed to make these connections.

Air is removed from the system by opening valve 22 for a sufficient length of time to permit flow through needle 14 to remove such air, after which knob 102 is rotated until diaphragm 36 is pressed down to block flow through aperture 66.

After needle 14 is inserted in the patient, for example, in arm 16, valve 22 is placed in its fully open position and knurled knob 102 is rotated until the drop count in chamber 20 reaches the prescribed rate.

Thereafter, orifice control diaphragm 34 will function to maintain constant the selected flow rate regardless of the changing level of liquid in the supply source, movement of reservoir 10 to a higher or lower position or raising or lowering of arm 16.

While in the figures diaphragms 34 and 36 are shown as undistorted, it should be understood that in normal operation of the apparatus, both of the aforementioned diaphragms will be bulging downwardly, diaphragm 34 to control flow through its orifice, and diaphragm 36 to block partially passageway 86.

Referring to FIG. 4 for a more detailed description of the operation within regulator 24, with diaphragm 36 pressed down into flared opening 82, flow is at the rate prescribed. From close examination of regulator 24 while in operation, it has been learned that membrane 64, instead of maintaining an equilibrium position based upon pressures within the inlet and outlet chambers, actually vibrates against bulge 54, opening and closing the orifice in sequence, in effect, pulsating, due presumably to buildup of pressure under diaphragm 64 followed by raising of the latter and drop in pressure. It is believed that this mode of operation may be caused by the relatively low rates of liquid flow through regulator 24 which would make it difficult to maintain the very small spacing of membrane 46 from the opening which would be required. In any event, it has been demonstrated that the arrangement as described maintains control over the flow within very narrow limits.

As the level of liquid 18 in reservoir 10 recedes there will be a tendency for flow to be reduced by the reduction in head involved. Pressure within the inlet chamber is reduced as the result of the reduction in head exerted within this chamber, and membrane 64 will adjust to increase the effective opening through the orifice opening into passageway 52 with a consequent compensating increase in flow. The raising of arm 16 will tend to decrease flow due to buildup of pressure within the outlet (lower) chamber, causing membrane 64 to increase the effective orifice opening producing a compensating increase in flow. Raising of reservoir 10 of lowering of arm 16 will similarly have the opposite effect on membrane 64 as just described, insuring compensating adjustments in the effective orifice opening. As previously mentioned, the flow rate through regulator 24 is altered by depressing knurled knob 102 to raise or lower screw member 98. Lowering of the latter will distort diaphragm 84 downwardly restricting further flow through passageway 86, and vice versa.

As an example of the effectiveness of the embodiment just described, it was found that as the head was varied between 24 and 42 inches the rate of liquid flow never varied over 0.5%.

Flow through regulator 24 can be terminated entirely by rotating knurled knob 102 until tip 99 of screw 98 forces diaphragm 36 down far enough to block entrance to passageway 86.

Figure 8:
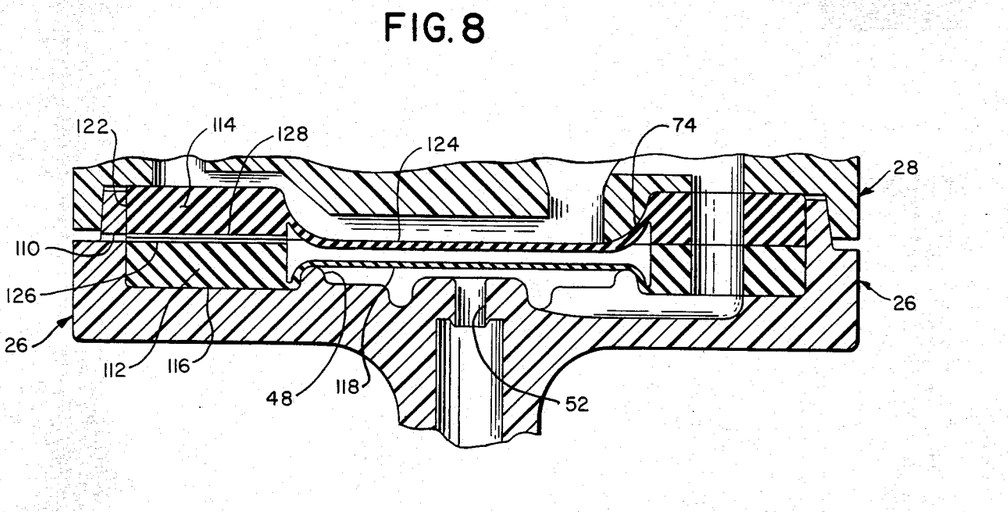
FIG. 8 is a partial view similar to that in FIG. 4 showing an alternative construction for the orifice control diaphragm.

In the event that membrane 64 should suffer a leak or a puncture, it is seen that all control over flow will effectively be gone. Although this is considered to be a remote possibility, an alternative construction to prevent such event from occurring, embodying the principles of this invention, is shown in FIG. 8. There it will be seen that cap 26 and main body 28 are assembled as shown in FIG. 4, but that the former is provided with an opening 110 whose purpose and location will be more fully described below.

Figure 9A:
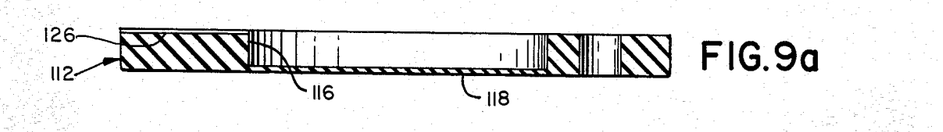
FIGS. 9a and 9b show section views of the unassembled parts of the diaphragm assembly seen in FIG. 8.
Figure 9B:
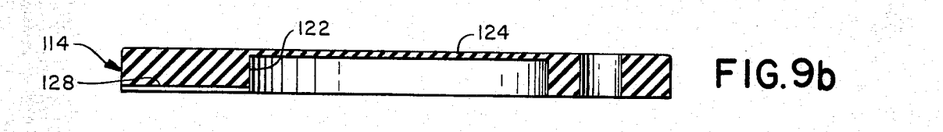
Figure 10:
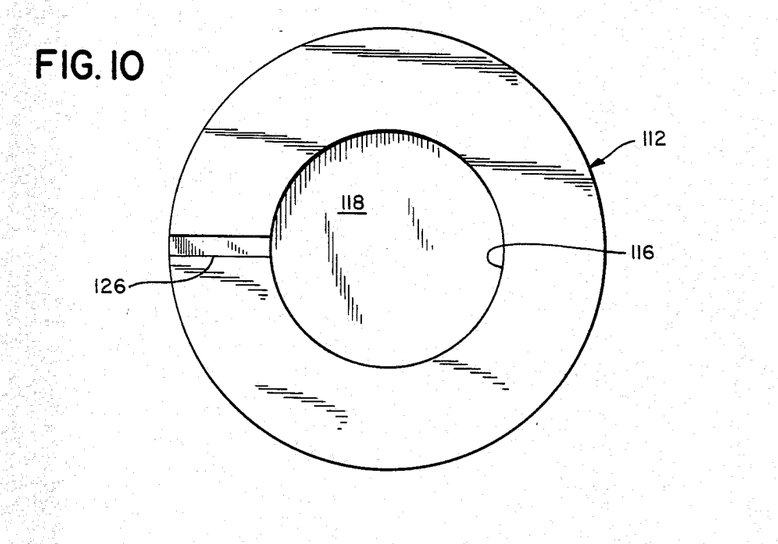

Instead of diaphragm 34, there is provided in its place a diaphragm assembly consisting of a pair of diaphragms 112 and 114, shown disassembled in FIGS. 9a and 9b, respectively. Diaphragm 112 is provided with an annular rim 116 and a thin membrane 118 spanning the opening. Diaphragm 114 is similarly provided with a rim 122 and a membrane 124. As also shown in FIG. 10, rims 116 and 122 are provided with a single, radially directed slot 126 and 128, respectively, so that when the two diaphragms 112 and 114 are properly assembled and aligned, as shown in FIG. 8, there is formed a passageway which is aligned with opening 110 in cap 26. Thus the chamber formed between membranes 118 and 124 is exposed to atmospheric pressure.

It will be noted that when diaphragms 112 and 114 are assembled within regulator 24, membrane 118 is rendered taut by bulge 48, while membrane 124 is stretched down and rendered taut by central section 74 of main body 28. Membranes 118 and 124 are spaced close to each other and, in this configuration, will not touch each other when regulator 24 is assembled. However, when the device is in use, membrane 124 will bulge downwardly under pressure from the liquid flowing above it, membrane 118 bulging upwardly, a sufficient distance to come into contact with each other, and in normal operation the two membranes will move in unison to maintain flow at a constant rate as described above.

If it is desired to have membranes 118 and 124 in contact with each other at all times, this may be accomplished by providing ribs or protuberances (not shown) on the surfaces facing each other high enough to insure this contact, while at the same time retaining exposure to atmospheric pressure.

Should one of the membranes 118 or 124 develop a leak, liquid 18 will merely flow out of regulator 24 through the passageway formed by slots 126 and 128, thereby preventing any injury to the patient.

The use of diaphragm 36 to control flow of liquid through passageway 86, as shown in FIG. 4, to establish the rate of flow through regulator 24, may under certain circumstances not provide the precise flow rate desired due to the flexible nature of the material from which it is made.

Figures 11, 14:
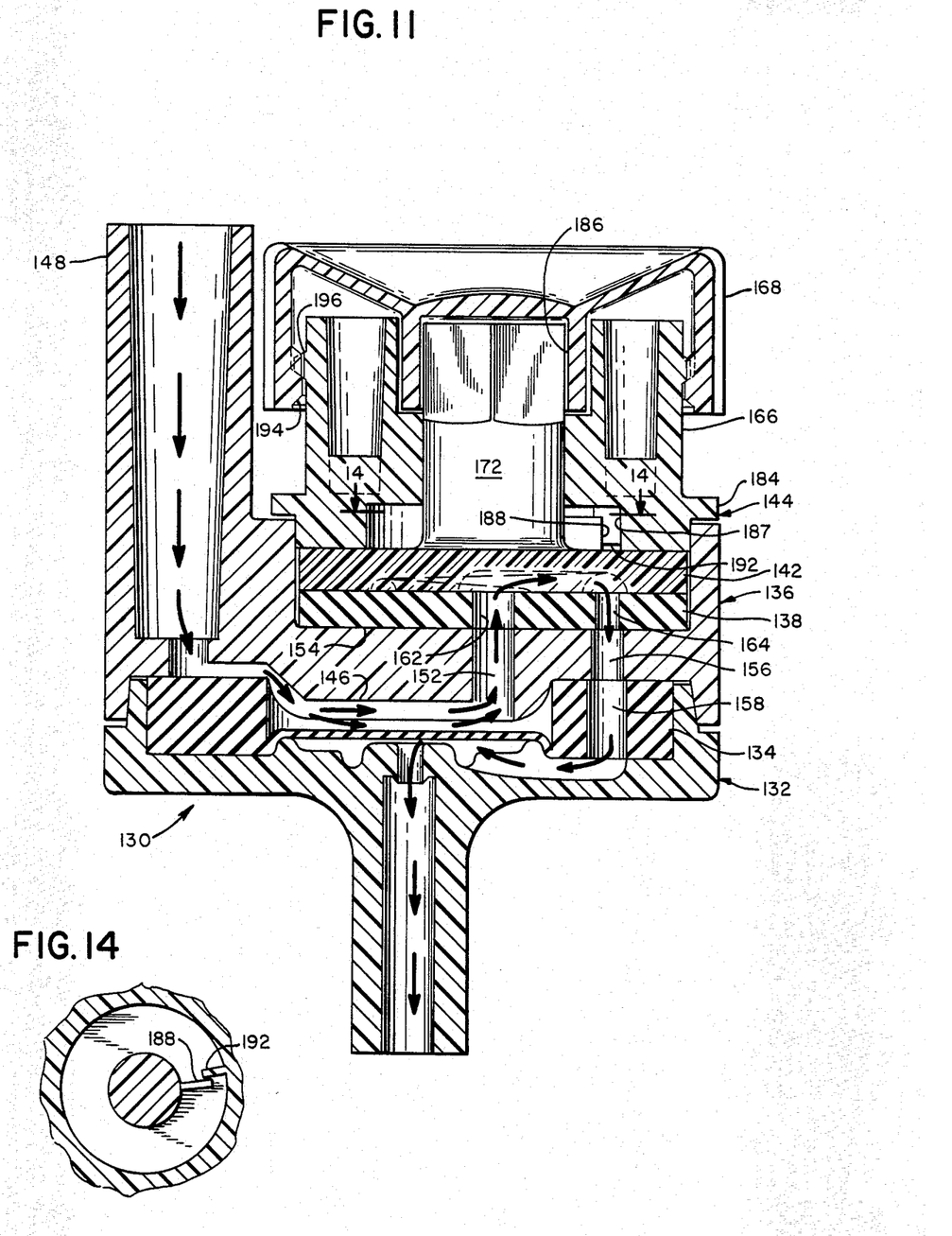
FIG. 11 is a view similar to that in FIG. 4 showing an alternative construction for the valve assembly.
FIG. 14 shows schematically the use of stops to limit rotation of the disc shown in FIGS. 11-13.
Figure 12:
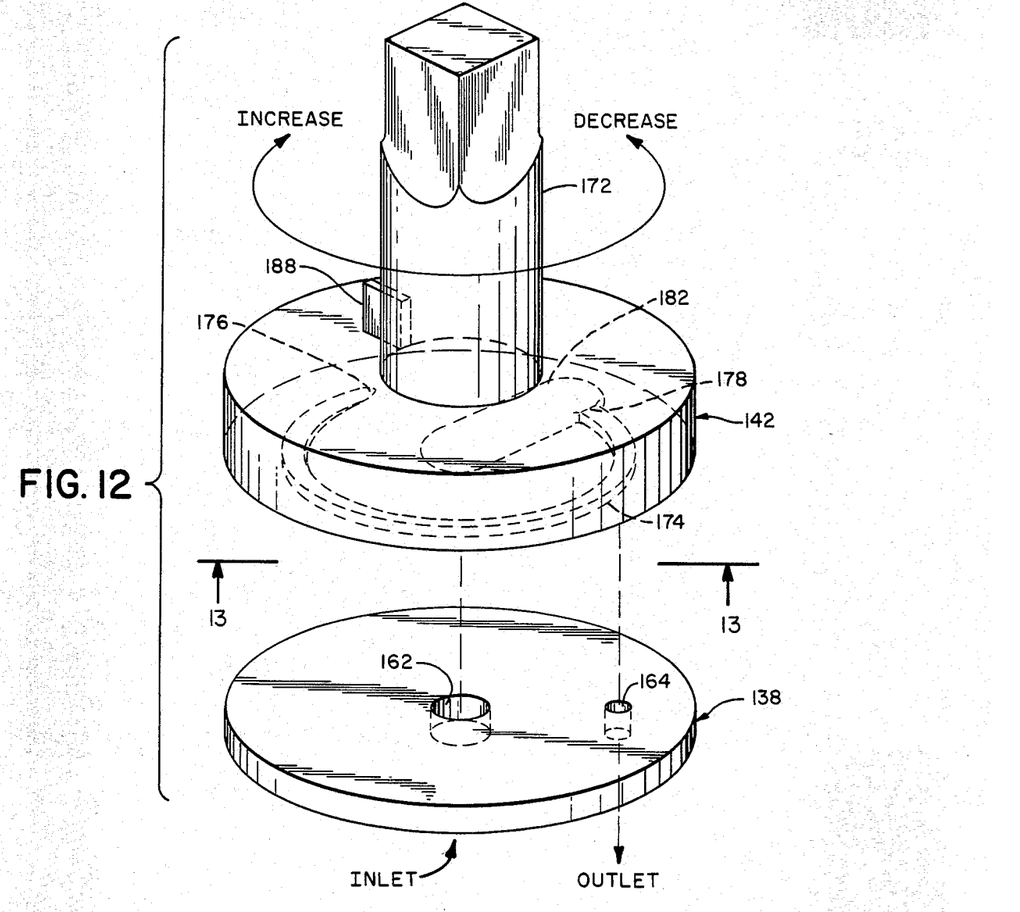
FIG. 12 is an exploded view of the grooved disk and flexible gasket shown in FIG. 11.
Figure 13:
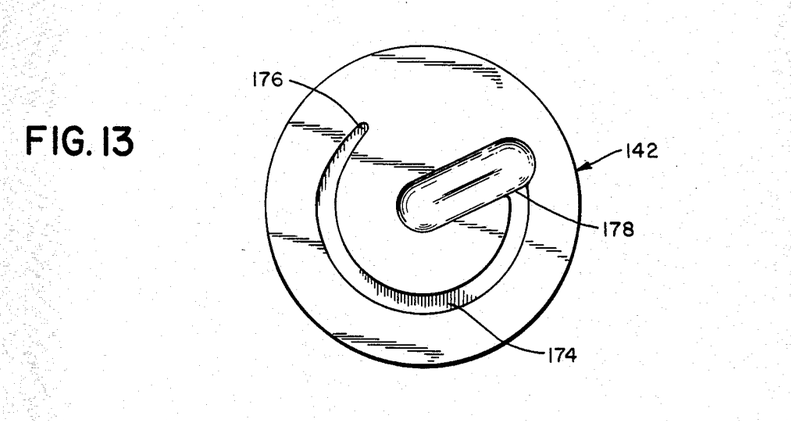
FIG. 13 is a bottom view of the grooved disc shown in FIG. 12.

An alternative valve arrangement for selecting the flow rate through passageway 86 is illustrated in FIGS. 11, 12, and 13.

As shown in FIG. 11, there is a regulator 130 similar to regulator 24 except for the changes about to be described. Regulator 130 consists of a diaphragm cap 132 similar to that of cap 26, a diaphragm 134 like that of diaphragm 34, a main body 136, a flexible gasket 138, a grooved disc 142, and a valve assembly 144. It is understood that the double diaphragm arrangement shown in FIGS. 8-10 could also be employed if desired instead of diaphragm 134.

Main body 136 has a radially extending channel 146 connecting inlet 148 to upwardly extending passageway 152. A flat surface 154 is provided for flexible gasket 138 and a transfer passageway 156 is aligned with aperture 158 in diaphragm 134. Gasket 138 in the shape of a flat circular disc has a pair of holes 162 and 164 aligned with passageways 152 and 156, respectively.

Valve assembly 144 consists of grooved disc 142 resting on gasket 138, a retainer 166, and a control knob 168.

For details of disc 142, reference is made to FIGS. 12 and 13. There it will be noted that disc 142 has an upwardly and axially extending shaft 172 terminating in a rectangular cross section. On the underside of disc 142 there is an annular channel 174 whose depth increases from a minimum or zero value at 176 to some maximum value at 178 where channel 174 communicates with a chamber 182 which is elongated in a radial direction, extending from channel 174 to the center of circular disc 142. It will thus be seen that when disc 142 is in contact with gasket 138, chamber 182 is always in communication with hole 162 and some portion of channel 174 is always in communication with hole 164 over its length. As disc 142 is rotated in either direction as indicated by the arrows, the depth of channel 174 opposite hole 164 establishes the effective opening for liquid flow. When disc 142 is rotated counterclockwise looking down so that the end 176 of channel 174 passes hole 164, then all flow is blocked. If disc is rotated clockwise until chamber 182 is opposite hole 164 there is maximum liquid flow, while points in between represent intermediate rates of flow. In this arrangement, it is readily seen that only a single turn or rotation of disc 142 adjusts flow from the maximum rate to zero, and selection of flow rate is precise.

Referring back to FIG. 11, retainer 166 has a central opening to accommodate shaft 172 of disc 142 and has a shoulder 184 to engage main body 136. When the parts are attached in the manner previously described in connection with regulator 24, disc 142 places gasket 138 under slight compression to reduce or eliminate any leakage of liquid between the parts.

Control knob 168 has a rectangular opening 186 to accommodate and engage the top of shaft 172 so that rotation of the former will cause rotation of the latter.

To limit the rotation of disc 142 to about one complete turn, retainer 166 is provided with an annular cut out 187 to provide clearance for protuberances 188 and 192 which may be provided to limit movement of disc 142 over the arc covered by channel 174 and chamber 182 as also shown in FIG. 14. Control knob 168 can be provided with markings on its top surface to indicate the various degrees of opening to flow using indicia located on a facing surface of inlet 148 or on surface of body 136 or assembly 144.

If knob 168 is made of flexible material then the use of protuberances 194 and 196 as previously described for regulator 24 may be employed to lock the position selected, necessitating that knob 168 be pressed down (as illustrated) to effect its rotation.

From the above description of the preferred embodiments it is seen that there has been provided a liquid flow regulator uniquely adaptable for use in mantaining constant the flow of liquids administered to patients. While the specific embodiments illustrated show its use with an I.V. system, it is readily seen that the regulator could be employed in connection with the administration of liquids other than intravenously, as, for example, liquids being introduced through an oral cavity or through the rectum, wherever and whenever the rate that the liquid being supplied is done so at a closely controlled constant rate.

Due to the very simple and inexpensive constructions of the regulators herein described, it is seen that they may be used only once and then discarded. Thus the regulators may be packaged in sterile condition for one time use.

It has also been noted that a regulator made in accordance with this invention is designed for use with gravitational feeds, or, in other words, relatively low liquid pressures. As a result of this feature, it has been found under certain conditions where a gravitational feed may not be available or convenient, such as when a patient is ambulatory or is being moved, a very slight pressure may be applied to the reservoir, containing the liquid, by hand, a weight, or a spring, and flow in the system will be maintained.

While only certain specific, preferred embodiments of the invention have been described, it is understood that many variations thereof are possible without departing from the principles of this invention as defined in the following claims.

What is claimed is:

1. Apparatus for administering liquid to a patient at a selected constant rate of flow comprising:
   a. means for being connected to said patient for the administration of said liquid;
   b. reservoir means for containing a supply of said liquid supported at an elevation sufficient to obtain gravitational force for the flow of said liquid;
   c. tube means for delivering said liquid from said reservoir means to said administration means; and
   d. regulator means in said tube means for selecting and maintaining a constant rate of flow of said liqid, comprising, a housing with inlet and outlet means for receiving and discharging said liquid, respectively, diaphragm means having a thickened rim with a central thin membrane within said housing for separating said inlet means from said outlet means and forming inlet and outlet chambers, respectively, said membrane having a surface contiguous with a surface on said thickened rim, means in said housing comprising an annular bulge contacting said surface on said membrane adjacent said thickened rim for stretching said membrane and insuring proper location and tautnesss of said membrane, said inlet means receiving said liquid from said reservoir means, said outlet means delivering said liquid to said administration means, orifice means for directing liquid from said outlet chamber into said outlet means, said diaphragm means supported within said housing to that said membrane effectively controls flow through said orifice means into said outlet means, passageway means bypassing said membrane for permitting flow of said liquid from said inlet chamber to said outlet chamber, and valve means for controlling flow through said passageway means, said valve means establishing the flow rate through the regulator means, said membrane in response to differential pressures exercised by liquid in said inlet and outlet chambers maintaining constant the flow rate of said liquid as selected by said valve means.

2. The apparatus of claim 1 in which said passageway means extends through the thickened rim of said diaphragm means.

3. Apparatus for establishing and maintaining constant the flow rate of liquid passing therethrough comprising:
   a. inlet and outlet means for receiving and discharging said liquid, respectively;
   b. diaphragm means having a thickened rim with a central membrane means consisting of a central thin section having one surface contiguous with one surface of said thickened rim for separating said inlet and outlet means and forming inlet and outlet chambers, respectively;
   c. orifice means for directing liquid from said outlet chamber into said outlet means;
   d. means for supporting said diaphragm means and stretching said membrane means comprising means to contact said central thin section adjacent said rim as said apparatus is assembled to insure proper location and tautness of said membrane means, said membrane means being positioned to control the flow of liquid through said orifice means into said outlet means;
   e. passageway means comprising an opening through the thickened rim of said diaphragm means bypassing said membrane means for permitting flow of said liquid from said inlet chamber to said outlet chamber; and
   f. valve means including means to restrict adjustably the flow through said opening for establishing a flow rate through said apparatus by controlling flow through said passageway means, said membrane means acting in response to differential pressure exercised by said liquid in said inlet and outlet chambers to maintain constant the flow rate established by said valve means.

4. Apparatus for administering liquid to a patient at a selected constant rate of flow comprising:
   a. means for being connected to said patient for the administration of said liquid;
   b. reservoir means for containing a supply of said liquid supported at an elevation sufficient to obtain gravitational force for the flow of said liquid;
   c. tube means for delivering said liquid from said reservoir means to said administration means;
   d. regulator means in said tube means for selecting and maintaining a constant rate of flow of said liquid, comprising, a housing with inlet and outlet means for receiving and discharging said liquid, respectively, diaphragm means having a thickened rim with a central thin membrane within said housing for separating said inlet means from said outlet means and forming inlet and outlet chambers, respectively, means in said housing for stretching said membrane taut, said inlet means receiving said liquid from said reservoir means, said outlet means delivering said liquid to said administration means, orifice means for directing liquid from said outlet chamber into said outlet means, said diaphragm means supported within said housing so that said membrane effectively controls flow through said orifice means into said outlet means, passageway means extending through the thickened rim of said diaphragm means bypassing said membrane for permitting flow of said liquid from said inlet chamber to said outlet chamber, and valve means for controlling flow through said passageway means, said valve means establishing the flow rate through the regulator means, said membrane in response to differential pressures exercised by liquid in said inlet and outlet chambers maintaining constant the flow rate of said liquid as selected by said valve means; and
   e. said diaphragm means including means to discharge said liquid out of said housing and away from said outlet means in the event said diaphragm means develops a leak thereby losing effective control over liquid flow.

5. The apparatus of claim 4 in which said diaphragm means includes a pair of spaced membranes with the space between said membranes vented, said membranes being in physical contact with each other during normal operation of said regulator.

6. Apparatus for administering liquid to a patient at a selected constant rate of flow comprising:
   a. means for being connected to said patient for the administration of said liquid;
   b. reservoir means for containing a supply of said liquid supported at an elevation sufficient to obtain gravitational force for the flow of said liquid;
   c. tube means for delivering said liquid from said reservoir means to said administration means;
   d. regulator means in said tube means for selecting and maintaining a constant rate of flow of said liquid, comprising, a housing with inlet and outlet means for receiving and discharging said liquid, respectively, diaphragm means having a thickened rim with a central thin membrane within said housing for separating said inlet means from said outlet means and forming inlet and outlet chambers, respectively, means in said housing for stretching said membrane taut, said inlet means receiving said liquid from said reservoir means, said outlet means delivering said liquid to said administration means, orifice means for directing liquid from said outlet chamber into said outlet means, said diaphragm means supported within said housing so that said membrane effectively controls flow through said orifice means into said outlet means, passageway means extending through the thickened rim of said diaphragm means bypassing said membrane for permitting flow of said liquid from said inlet chamber to said outlet chamber, and valve means for controlling flow through said passageway means, said valve means establishing the flow rate through the regulator means, said membrane in response to differential pressures exercised by liquid in said inlet and outlet chambers maintaining constant the flow rate of said liquid as selected by said valve means; and e. said valve means including a flat member having a pair of spaced holes through which said liquid flows in opposite directions, and rotatable disc means in contact with one flat surface of said member having an annular groove of variable depth providing communication between said holes for flow of said liquid, rotation of said disc means adjusting the effective opening between said holes thereby permitting selection of the rate of flow of liquid therethrough.

7. Apparatus for establishing and maintaining constant the flow rate of liquid passing therethrough comprising:

a. inlet and outlet means for receiving and discharging said liquid, respectively;

b. diaphragm means having a thickened rim with a central membrane means for separating said inlet and outlet means and forming inlet and outlet chambers, respectively;

c. orifice means for directing liquid from said outlet chamber into said outlet means;

d. means for supporting said diaphragm means and pulling said membrane means taut, said membrane means being positioned to control the flow of liquid through said orifice means into said outlet means;

e. passageway means extending through said diaphragm means bypassing said membrane means for permitting flow of said liquid from said inlet chamber to said outlet chamber;

f. valve means for establishing a flow rate through said apparatus by controlling flow through said passageway means, said membrane means acting in response to differential pressure exercised by said liquid in said inlet and outlet chambers to maintain constant the flow rate established by said valve means;

g. said diaphragm means consisting of the aforesaid thickened rim and a central thin section comprising said membrane means, said passageway means including an opening through said rim for the flow of said liquid;

h. said passageway means including a passage aligned with and extending from said opening to said inlet chamber, said valve means including means to restrict adjustably flow through said passage; and i. said valve means including a diaphragm forming a part of said passage and means to distort said diaphragm to regulate flow through said passage.

8. Apparatus for establishing and maintaining constant the flow rate of liquid passing therethrough comprising:

a. inlet and outlet means for receiving and discharging said liquid, respectively;

b. diaphragm means having a thickened rim with a central membrane means for separating said inlet and outlet means and forming inlet and outlet chambers, respectively;

c. orifice means for directing liquid from said outlet chamber into said outlet means;

d. means for supporting said diaphragm means and pulling said membrane means taut, said membrane means being positioned to control the flow of liquid through said orifice means into said outlet means;

e. passageway means extending through said diaphragm means bypassing said membrane means for permitting flow of said liquid from said inlet chamber to said outlet chamber;

f. valve means for establishing a flow rate through said apparatus by controlling flow through said passageway means, said membrane means acting in response to differential pressure exercised by said liquid in said inlet and outlet chambers to maintain constant the flow rate established by said valve means; and g. said diaphragm means including means to discharge said liquid from said apparatus bypassing said outlet means in the event said membrane means develops a leak thereby losing effective control over liquid flow.

9. The apparatus of claim 8 in which the membrane means includes a pair of spaced membranes with the space between said membranes vented, said membranes coming into physical contact with each other during normal operation of said apparatus.

10. Apparatus for establishing and maintaining constant the flow rate of liquid passing therethrough comprising:

a. inlet and outlet means for receiving and discharng said liquid, respectively;

b. diaphragm means having a thickened rim with a central membrane means for separating said inlet and outlet means and forming inlet and outlet chambers, respectively;

c. orifice means for directing liquid from said outlet chamber into said outlet means;

d. means for supporting said diaphragm means and pulling said membrane means taut, said membrane means being positioned to control the flow of liquid through said orifice means into said outlet means;

e. passageway means extending through said diaphragm means bypassing said membrane means for permitting flow of said liquid from said inlet chamber to said outlet chamber;

f. valve means for establishing a flow rate through said apparatus by controlling flow through said passageway means, said membrane means acting in response to differential pressure exercised by said liquid in said inlet and outlet chambers to maintain constant the flow rate established by said valve means; and g. said valve means comprising a flat member having a pair of holes communicating and in series with said passageway means, rotatable disc means in contact with one flat surface of said member having a groove of variable depth providing communication between said holes for flow of said liquid, and means to rotate said disc means to adjust the effective opening between said holes through said disc in order to establish the rate of flow through said passageway means.

11. The apparatus of claim 10 having means to limit the rotation of said disc means to about one complete turn over which flow is selectable to between no flow and maximum flow.

* * * * *